(12) United States Patent
Tu

(10) Patent No.: US 7,470,276 B2
(45) Date of Patent: Dec. 30, 2008

(54) MULTIFUNCTIONAL FORCEPS SET AND LOOP LIGATURE CO-USED THEREWITH

(76) Inventor: Fung-Chao Tu, 7F-4, No. 7, Lane 144, Nan Ya S. Road, Ban Chiao City, Taipei Hsien (TW)

( * ) Notice: Subject to any disclaimer, the term of this patent is extended or adjusted under 35 U.S.C. 154(b) by 737 days.

(21) Appl. No.: 10/642,782

(22) Filed: Aug. 19, 2003

(65) Prior Publication Data

US 2005/0043744 A1   Feb. 24, 2005

(51) Int. Cl.
*A61B 17/04* (2006.01)
*A61B 17/00* (2006.01)
*A61B 17/32* (2006.01)

(52) U.S. Cl. .................. 606/144; 606/205; 606/170

(58) Field of Classification Search .............. 606/139, 606/206, 148, 140–144, 205–207
See application file for complete search history.

(56) References Cited

U.S. PATENT DOCUMENTS

| | | | | |
|---|---|---|---|---|
| 5,542,949 A | * | 8/1996 | Yoon | 606/143 |
| 5,704,943 A | * | 1/1998 | Yoon et al. | 606/139 |
| 5,728,112 A | * | 3/1998 | Yoon | 606/144 |
| 5,830,231 A | * | 11/1998 | Geiges, Jr. | 606/205 |
| 5,843,099 A | * | 12/1998 | Nichols et al. | 606/144 |
| 6,520,960 B2 | * | 2/2003 | Blocher et al. | 606/51 |
| 6,635,065 B2 | * | 10/2003 | Burbank et al. | 606/148 |

* cited by examiner

*Primary Examiner*—Todd E. Manahan
*Assistant Examiner*—Diane Yabut
(74) *Attorney, Agent, or Firm*—Troxell Law Office, PLLC

(57) ABSTRACT

A multifunctional forceps set which integrates two important surgical procedures of incision and ligation into a continuous working procedure. The forceps set is co-used with two loop ligatures formed of braided sutures and transfigured from a surgeon's knot. In use, the loop ligatures are side by side loaded in the forceps mouth of the forceps and controlled by the forceps to minify the size of the loop and accomplish ligation function. The forceps set is developed from consolidation of surgical scalpel, forceps and device simulating finger's functions. Also, the forceps set can rapidly perform the procedures of double grasping, incision between grasping, proper ligating divided pedicles and cutting residual sutures of post-ligation. The forceps set enables surgeons to use familiar technique in a challenging operative field such as endoscopic surgery.

22 Claims, 16 Drawing Sheets

US 7,470,276 B2

MULTIFUNCTIONAL FORCEPS SET AND LOOP LIGATURE CO-USED THEREWITH

BACKGROUND OF THE INVENTION

The present invention is related to an operation instrument, and more particularly to a multifunctional forceps set which is designed from the key concept of integrating surgical procedures of double grasping, incision and ligation into a continuous working procedure to facilitate progress of operation. The forceps set of the present invention can be easily solely operated by an operator.

Surgeon uses surgical scalpel for excision, hemostatic forceps for bleeding control, suture for ligation bleeding vessels or vascular pedicles in his or her routine surgical procedures. However, it's hard to do it in a confined operation field like endoscopic surgery. To accomplish these important and necessary operative procedures, it has to depend on alternative devices such as metallic clips, stapler, Roeder loop ligature and equipment using special energy sources such as electro-surgery units, laser or harmonic scalpel, etc. All of these instruments or devices are extremely expensive and have their inherent limitations in real practice. The laser or harmonic scalpel can coagulate small vessels only (diameter less than 4 mm). The bipolar electro-surgery device that is extensively used in current endoscopic surgery can provide better coagulation for large vessels, but may cause more peripheral thermal tissue injury. Ligasure™, a new bipolar electro-surgery unit has the features of high ampere, low voltage and low thermal injury can coagulate larger vessels with diameter up to 7 mm. However, a common silk suture can ligate a vessel with diameter up to 10 mm easily. Metallic clips and staplers can clip vessels or seal vascular tissue, but will cause permanent foreign body retention effect on tissue. Roeder loop ligature is not convenient to use and does not have enough tensile strength in bulky ligation. In addition, it will cost a new user much time to learn the use of the above instruments or devices. Furthermore, in case these instruments are incorrectly used, a seriously dangerous result may occur. The limited performance of those alternative instruments or devices points to the urgent need for the better and safer instrument in real practice.

SUMMARY OF THE INVENTION

It is therefore a primary object of the present invention to provide a multifunctional forceps set, the multifunctional forceps set can be very easily and safely operated, enabling surgeons to perform surgery in confined and challenging operation field.

The present invention can be best understood through the following description and accompanying drawings wherein:

DETAILED DESCRIPTION OF THE PREFERRED EMBODIMENTS

Figure 7:
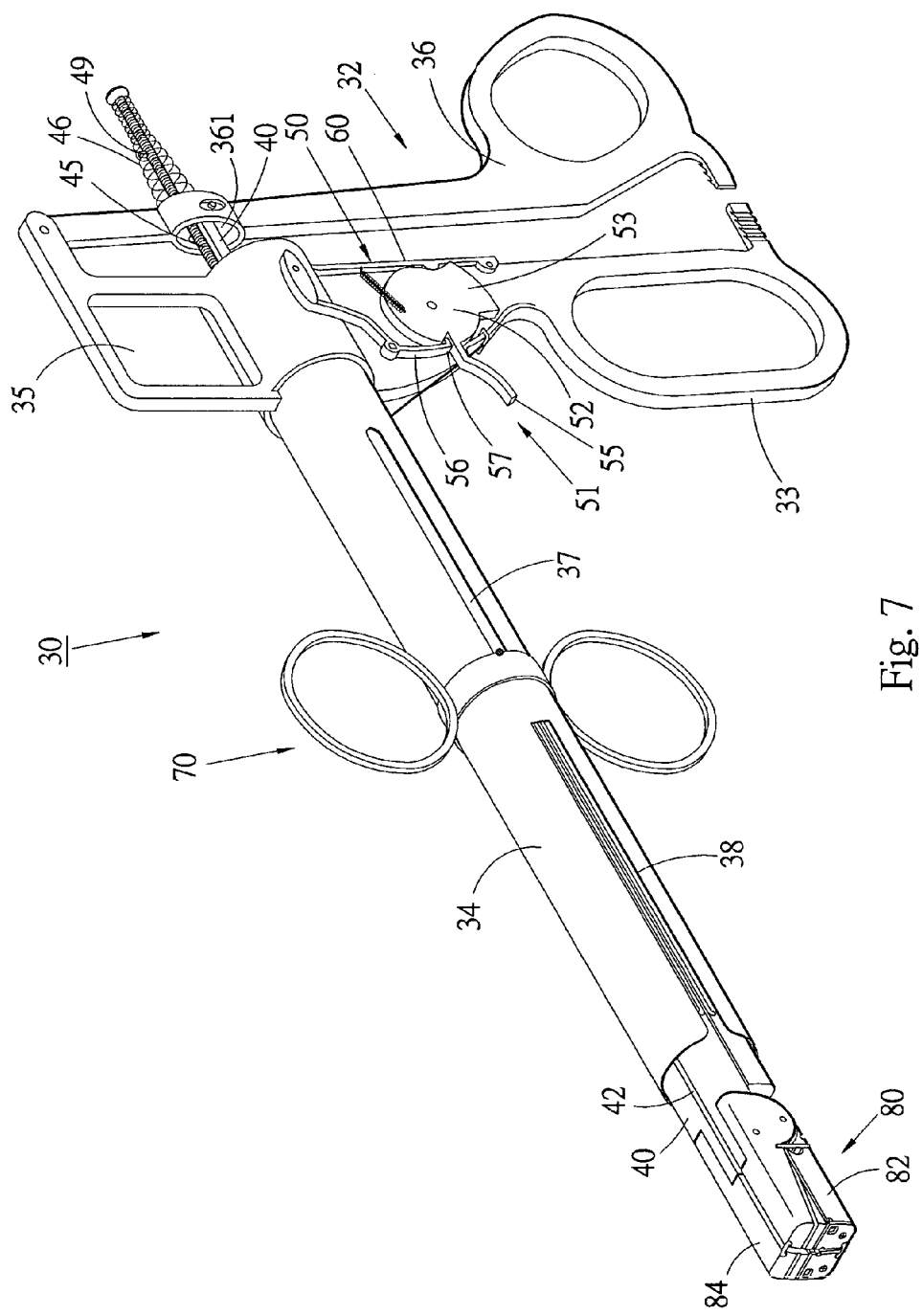
FIG. 7 is a perspective assembled view of a preferred embodiment of the forceps set of the present invention.

FIG. 7 shows a preferred embodiment of the multifunctional forceps set of the present invention which includes a forceps and two loop ligatures disposed on the forceps.

Figure 1:
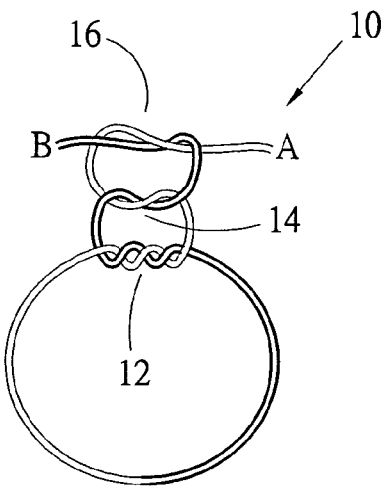
FIG. 1 is a perspective view showing the structure of a standard surgeon's knot.
Figure 2:
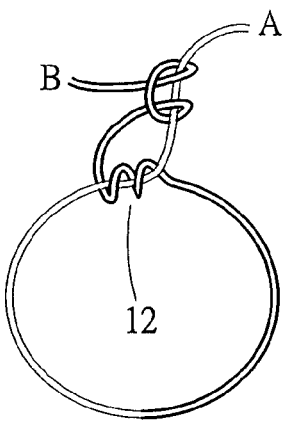
FIG. 2 shows that the standard surgeon's knot is converted into the loop ligature of the present invention.
Figure 3:
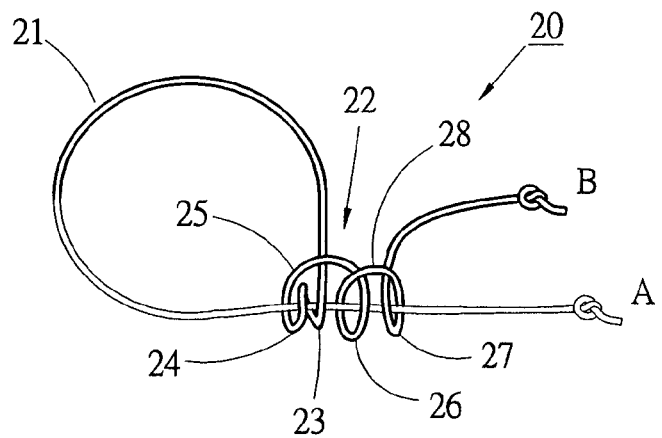
FIG. 3 shows the structure of the loop ligature of the present invention.

FIG. 3 shows the configuration of the loop ligature 20. The loop ligature 20 is transfigured from a standard surgeon's knot. FIG. 1 shows a standard surgeon's knot 10 for ligating a tissue such as a vessel. The surgeon's knot is braided from a surgical braided and coated suture. (In this embodiment, USP "0" braided and coated polyglactin 910 is chosen as standard reference.) The standard surgeon's knot 10 includes a twice matted section 12, a first once matted section 14 on outer side and a second once matted section 16 on outermost side. When the segment A of the surgeon's knot 10 is pulled to straighten the two once matted sections 14, 16, a state as shown in FIG. 2 is formed. Then the segment A of the surgeon's knot 10 is pulled to straighten the twice matted section 12, whereby the loop ligature 20 transfigured from the surgeon's knot is formed as shown in FIG. 3. The loop ligature 20 includes a loop 21 and a knotted section 22. The knotted section 22 has multiple circle sections formed by winding segment B around the segment A. The segment B is first wound around the segment A from one side of the loop 21 to form a first circle 23. Then the segment B is wound around the segment A from one side of the first circle section 23 near the loop 21 to form a second circle section 24. A first bridge section 25 extending from the second circle section 24 is bridged over the first circle section 23. Then a third circle section 26 is formed on the other side of the first circle section 23. Then a fourth circle section 27 is formed on a free side of the third circle section 26. A second bridge section 28 is bridged between the third and fourth circle sections 26, 27.

Figure 4:
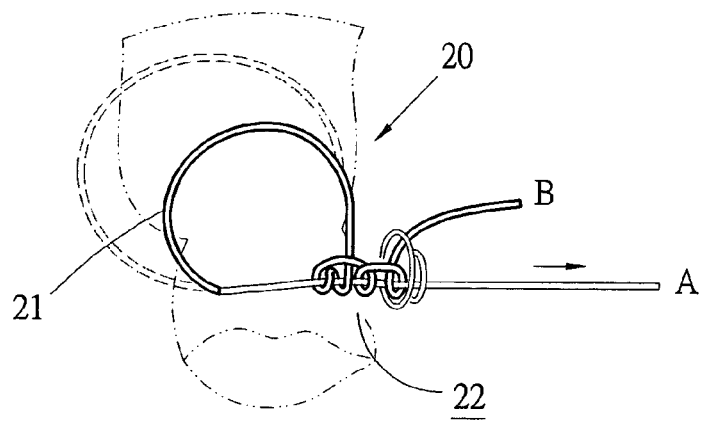
FIG. 4 shows that the loop of the loop ligature of the present invention is adjustable in size.
Figure 5:
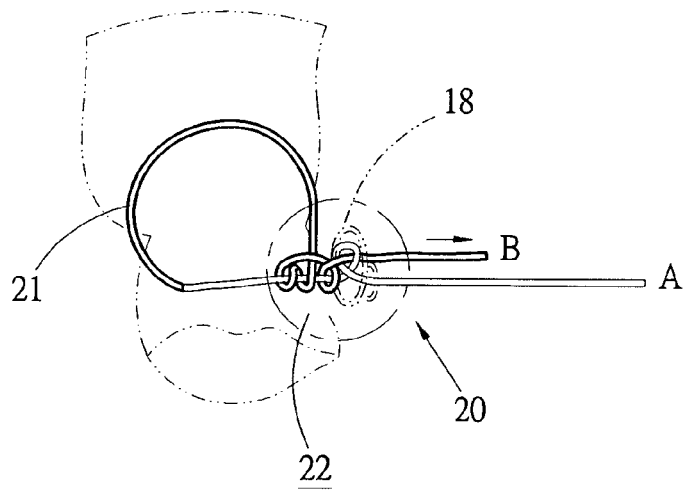
FIG. 5 shows that the loop ligature of the present invention is converted into a secure knot.
Figure 6:
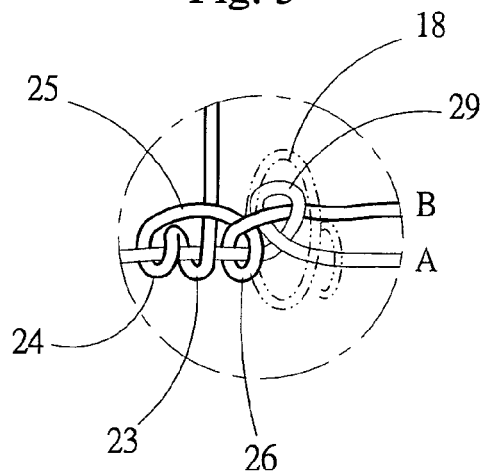
FIG. 6 is an enlarged view of circled area of FIG. 5.

The use of the loop ligature is different from the use of the common standard surgeon's knot. With respect to the standard surgeon's knot, two ends of the suture (the ends A and B shown in FIG. 1) are tracked to convert the matted sections 12, 14, 16 into a secure knot. In comparison with the standard surgeon's knot, the loop ligature of the present invention has two characteristics as follows:

1. The loop ligature 20 is not a secure knot. Instead, the loop ligature 20 is a slippery knot. With the knotted section 22 located, for example, when the knotted section 22 is pinched by fingers or when the loop ligature is fitted through a body having an opening (such as the ring body 18 shown in FIGS. 4 to 6) and the knotted section 22 is stopped and located, by means of tracking the movable end A, the diameter of the loop 21 can be changed.
2. After the loop 21 is adjusted to a suitable diameter, as shown in FIG. 5, the fixed end B is forcedly tracked to straighten the fourth circle section 27 of the knotted section 22, whereby the segment A is forcedly formed with a knotted section 29 tightly binding the segment B as shown in FIG. 5. Accordingly, the loop ligature 20 forms a firm secure knot. Therefore, the loop 21 cannot be expanded to achieve a binding effect. It is found through tests that the secure knot has a tensile strength of ligation as the standard surgeon's knot.

It should be noted that in the figures, the knotted section 22 is enlarged for illustration. In fact, the knotted section 22 is a tight state.

Figure 8:
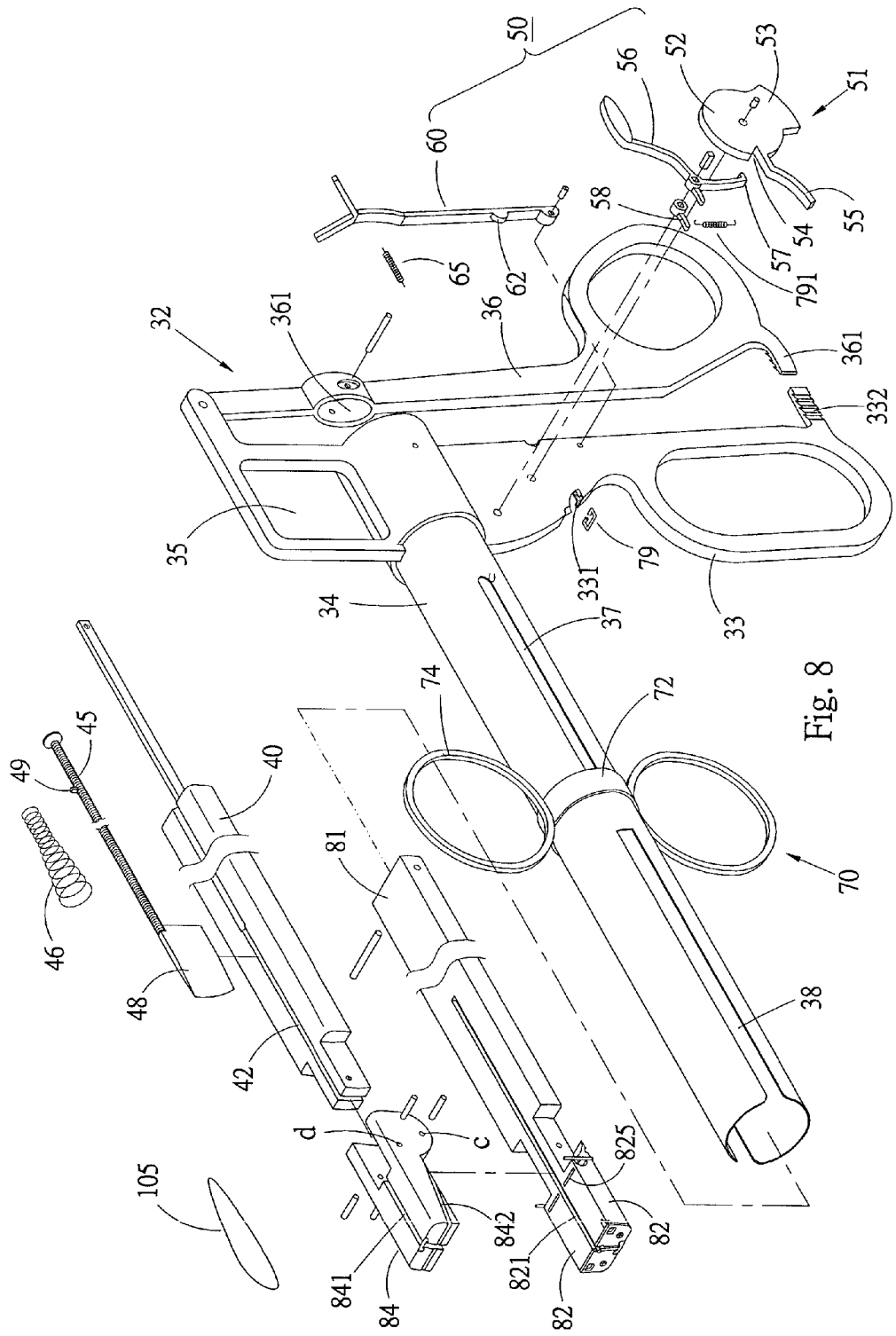
FIG. 8 is a general perspective exploded view of the preferred embodiment of the forceps set of the present invention according to FIG. 7.

Referring to FIGS. 7 and 8, the forceps set 30 of the present invention includes the following elements.

A forceps body 32 has a fixed handle 33 and a movable handle 36. A forward extending barrel 34 is disposed on upper side of the fixed handle 33. A finger hole 35 is formed on upper side of the barrel 34. A top end of the movable handle 36 is pivotally connected with a top end of the fixed handle 33 and positioned on rear side of the fixed handle 33. The movable handle 36 can be opened from the fixed handle 33 or closed to the fixed handle 33. The movable handle 36 is formed with a through hole 361 aligned with a rear end of the barrel 34. A pair of slots 37 are axially formed on the circumference of a middle section of the barrel 34. A pair of splits 38 are axially formed on two sides of front end of the barrel 34.

Figure 9:
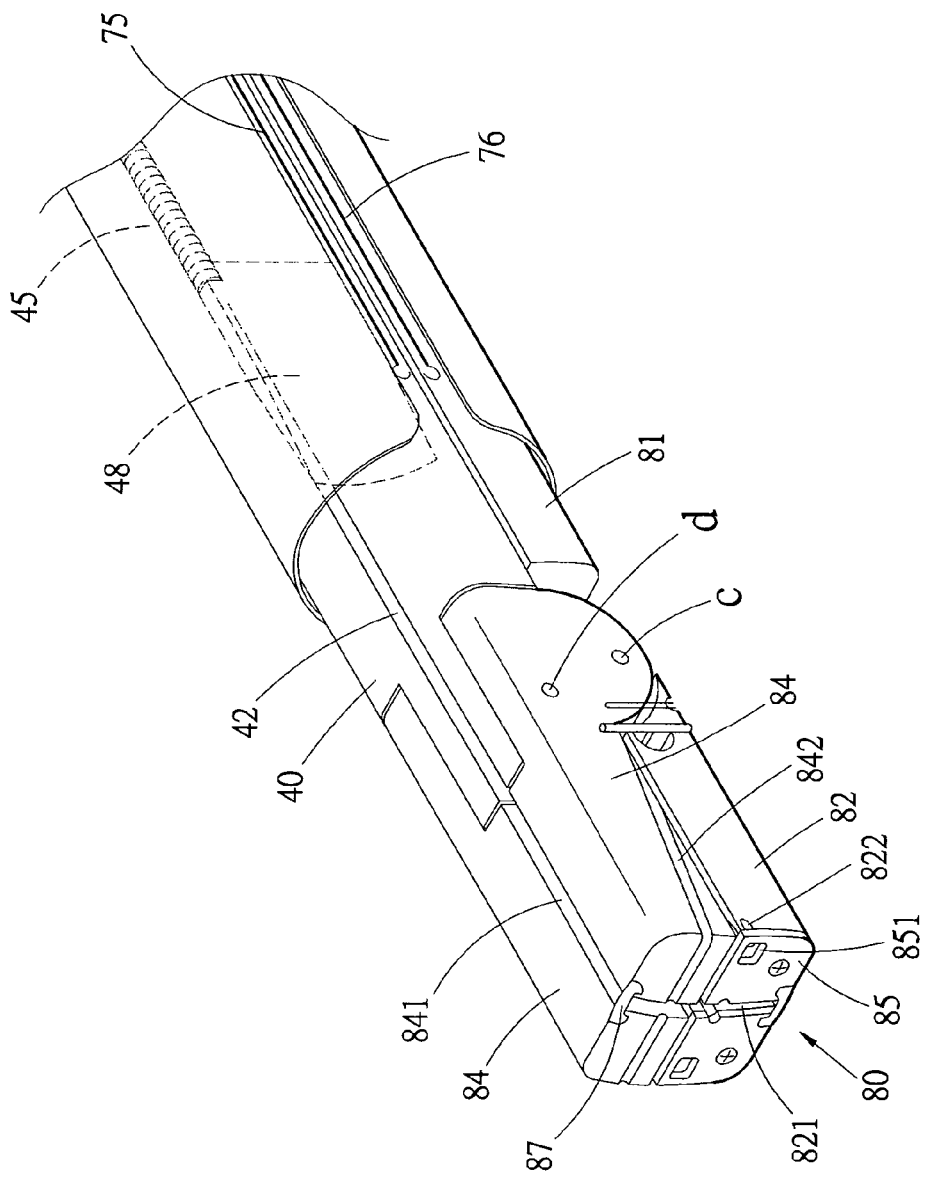
FIG. 9 is a perspective view of a front section of FIG. 7.

A first link 40 and a second link 45 are axially slidably fitted in the barrel 34. The front ends of the two links protrude from the front end of the barrel. The rear end of the first link 40 is pivotally connected in the through hole 361 of the movable handle 36. The rear end of the second link 45 extends through the through hole 361 and rearward protrudes from the movable handle. A first resilient member 46 is fitted on the second link 45. One end of the first resilient member 46 abuts against the rear end of the second link, while the other end of the first resilient member 46 abuts against the movable handle, whereby when no external force is applied to the second link, the second link keeps in a rearward position. A fissure 42 is axially formed on the first link 40 and inward extends from front end thereof. A blade 48 is fixed at front end of the second link 45. The second link 45 is placed on top face of the first link 40 with the blade 48 snugly positioned in the fissure 42 as shown in FIG. 9.

A press unit 50, in this embodiment, includes a trigger 51 and a lever 60.

The trigger 51 has a disc-shaped body section 52 and a pull arm 55 connected with the circumference of the body section. A cam section 53 is formed on the circumference of the body section. The body section of the trigger 51 is pivotally disposed on the forceps body, whereby the trigger 51 can be rotated. The pull arm 55 forward projects from front edge of the forceps body for manually shifting.

A secure pin 56 is angularly displaceably pivotally disposed on the forceps body. One end of the secure pin 56 has a hook section 57. When the secure pin is positioned in a latching position, the hook section hooks a notch 54 of the trigger to prevent the trigger from rotating.

The bottom end of the lever 60 is pivotally disposed on the fixed handle 33 behind the trigger 51, whereby the lever 60 can be swung. A second resilient member 65 is connected between the trigger and the lever. When no external force is applied to the lever, the second resilient member 65 on one hand resiliently keeps the lever in a forward leaning state and on the other hand keeps the trigger in a not pulled position. The lever 60 is formed with a protuberance 62 in contact with the body section 52 of the trigger. When pulling the trigger, the cam section 53 can drive the protuberance 62 of the lever 60 to make the free end of the lever swing forward. It should be noted that the configuration of the trigger is not limited to the conformation shown in the figures. Alternatively, a trigger can be back and forth slidably mounted on the forceps body. By means of rearward pressing the trigger, the rear end of the trigger can also push the lever to move backward.

A pull ring 70 has a ring body 72 and two ring sections 74 respectively fixedly connected with top and bottom end of the ring body. The ring body 72 is slidably fitted around the barrel 34.

Figure 10:
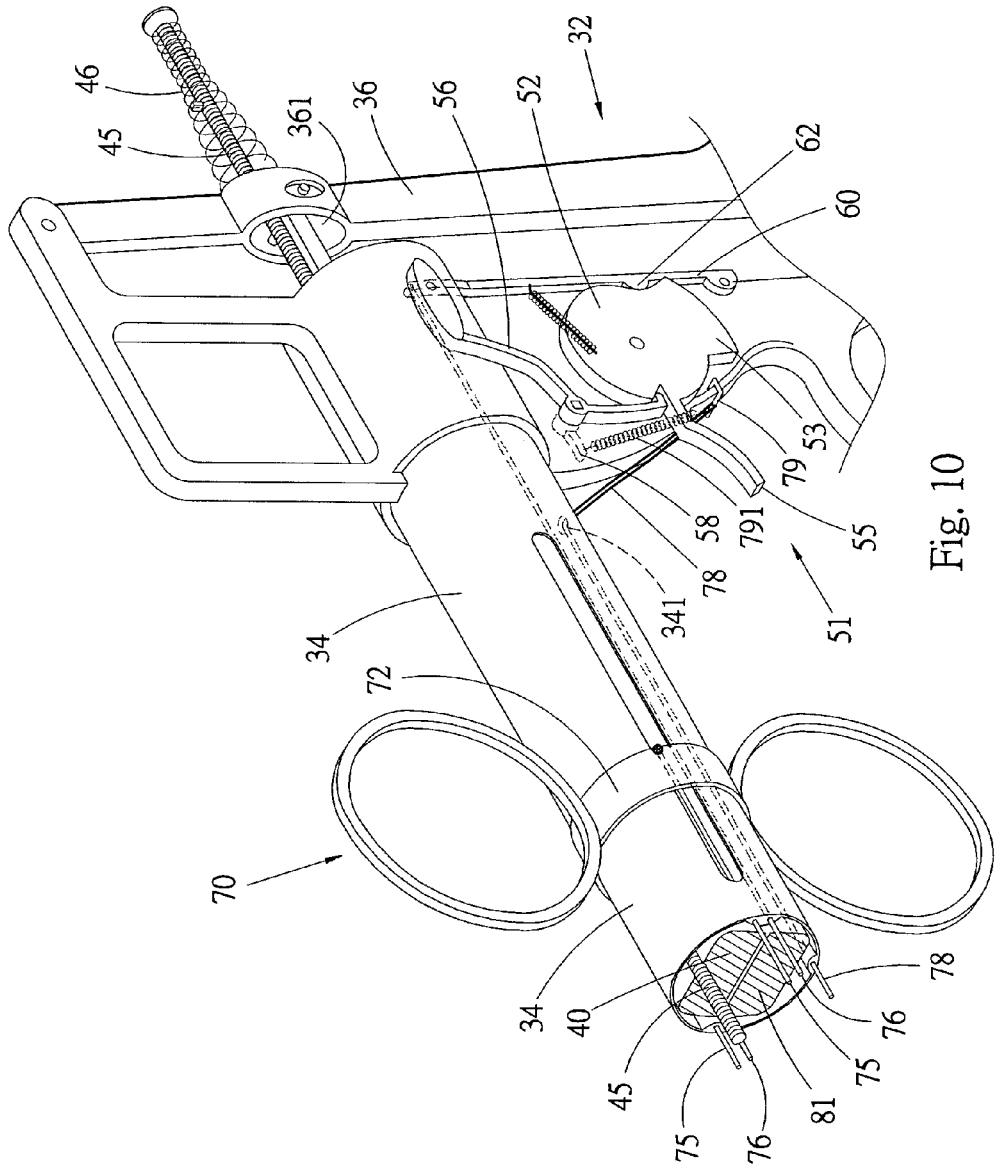
FIG. 10 is a perspective view of a rear section of the forceps set of the present invention.

Two first tracking members 75, two second tracking members 76 and a third tracking member 78 as shown in FIGS. 9 and 10. The tracking members are preferably steel strings and back and forth slidably disposed in the barrel 34. The two first and second tracking members 75, 76 are respectively positioned on two sides of the barrel. The third tracking member 78 is positioned on bottom side of the barrel. It should be noted that the portions of the wall of the barrel where the tracking members 75, 76, 78 and the second link 45 are disposed can be thickened. The thickened portions can be formed with fine tunnels through which the above members are passed.

The rear ends of the two first tracking members 75 are respectively fixedly disposed on two sides of the ring body 72 of the pull ring as shown in FIG. 10, whereby the first tracking members 75 can be pulled by the pull ring. The rear ends of the two second tracking members 76 are connected with the free end of the lever 60 to be pulled by the lever. The front ends of the first and second tracking members 75, 76 are exposed to outer side through the splits 38 of the barrel 34 as shown in FIGS. 7 and 9. The bottom of the barrel 34 is formed with an orifice 341 near the forceps body 32. The rear end of the third tracking member 78 is threaded through the orifice 341 and conducted out to connect with a connecting button 79 disposed on the forceps body. The connecting button 79 is up and down movably disposed on the fixed handle 33. In this embodiment, the front edge of the fixed handle is formed with a guide rail 331 the cross-section of which is T-shaped as shown in FIG. 8. The connecting button 79 is a U-shaped member up and down movably inlaid in the guide rail. However, the up and down moving measure of the connecting button is not limited to this embodiment. The present invention further includes a third connecting member 791. Referring to FIGS. 8 and 10, one end of the third resilient member 791 is connected with the connecting button 79, while the other end of the third resilient member 791 is connected with a connecting section 58. The connecting section 58 is a part of the secure pin 56 and is synchronously movable along with the secure pin 56. The third resilient member 791 resiliently keeps the secure pin in the latching position and keeps the connecting button 79 in an upper dead end of its travel. When the connecting button 79 is positioned in the upper dead end, the connecting button is right positioned under the pull arm 55 of the trigger.

A forceps mouth 80 has two side by side arranged lower jaws 82 and two side by side arranged upper jaws 84. In this embodiment, the two lower jaws 82 are integrally formed at front end of a bar member 81. The two lower jaws define therebetween a gap 821. The bar member 81 is fixedly fitted in the barrel from front end thereof with the two lower jaws 82 positioned at front end of the barrel. The bar member 81 is positioned under the first link 40. The rear end of each of the two upper jaws 84 has two pivot points c, d. The lower pivot point c serves as a fulcrum for pivotally connecting the upper jaw with the bar member 81. The upper pivot point d is for pivotally connecting the upper jaw with the front end of the first link 40. Accordingly, the upper jaws are pivotally connected with the two lower jaws on upper side thereof. When the first link is displaced to drivingly move the upper jaws 84, the upper jaws can be opened from the lower jaws or closed thereto. In addition, the front ends of the upper jaws can be fixed together by a staple 87 so as to ensure that the upper jaws be harmonically opened and closed. The upper jaws define a gap 841 therebetween. The gaps 821, 841 and the fissure 42 of the first link are in the same axial direction.

Figure 11:
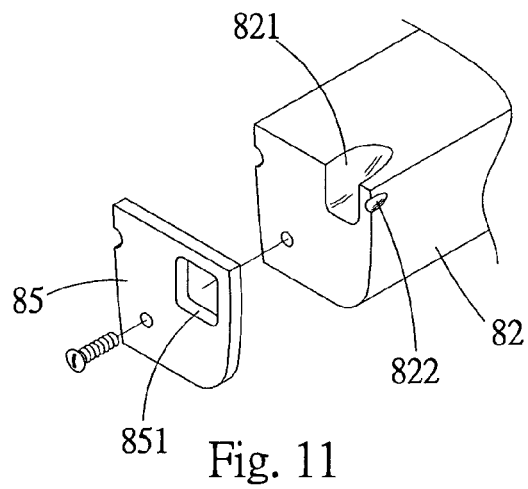
FIG. 11 shows the structure of front end of the lower jaw of the forceps set of the present invention.
Figure 12:
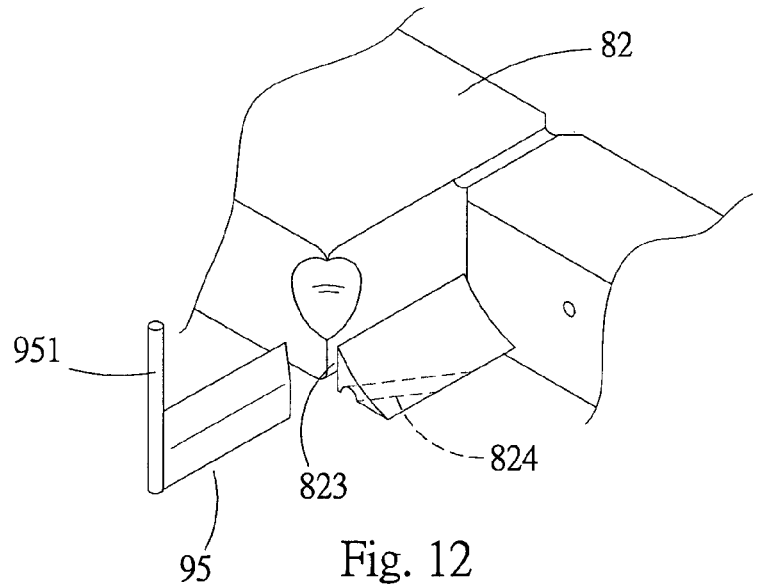
FIG. 12 shows the structure of rear end of the lower jaw of the forceps set of the present invention.

In addition, the periphery of each upper jaw 84 is formed with a circumferential groove 842. Referring to FIG. 11, the top edge of the front end of each lower jaw 82 is formed with a funnel-shaped recess 821 which is slightly larger than the volume of the knotted section 22 of the loop ligature 20. In addition, the front edge of outer side of each lower jaw is formed with a small groove 822 near the recess 821. The small groove 822 is slightly larger than the diameter of the suture. Two steel plates 85 are respectively fixedly disposed at front ends of the two lower jaws 82. Each steel plate 85 has a through hole 851 corresponding to the recess 821. Referring to FIG. 12, the outer side of rear end of each lower jaw 82 is formed with an inward extending small fissure 823 near the pivot joint. The bottom face of the rear end of the lower jaw is formed with a guide channel 824 behind the small fissure 823.

Figure 13:
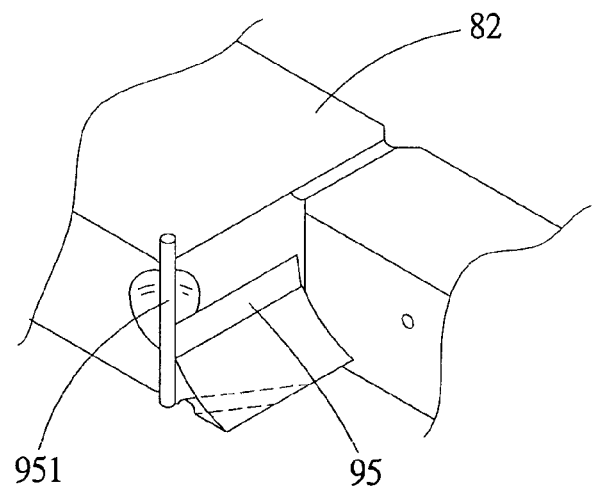
FIG. 13 is a view according to FIG. 12, showing that the small blade is mounted at rear end of the lower jaw.

The present invention further includes two small blades 95. As shown in FIGS. 12 and 13, the blade sections of the small blades face upward. The two small blades are respectively replaceably plugged in the two small fissures 823. A protective jacket 951 is disposed at outer end of each small blade.

Figure 14:
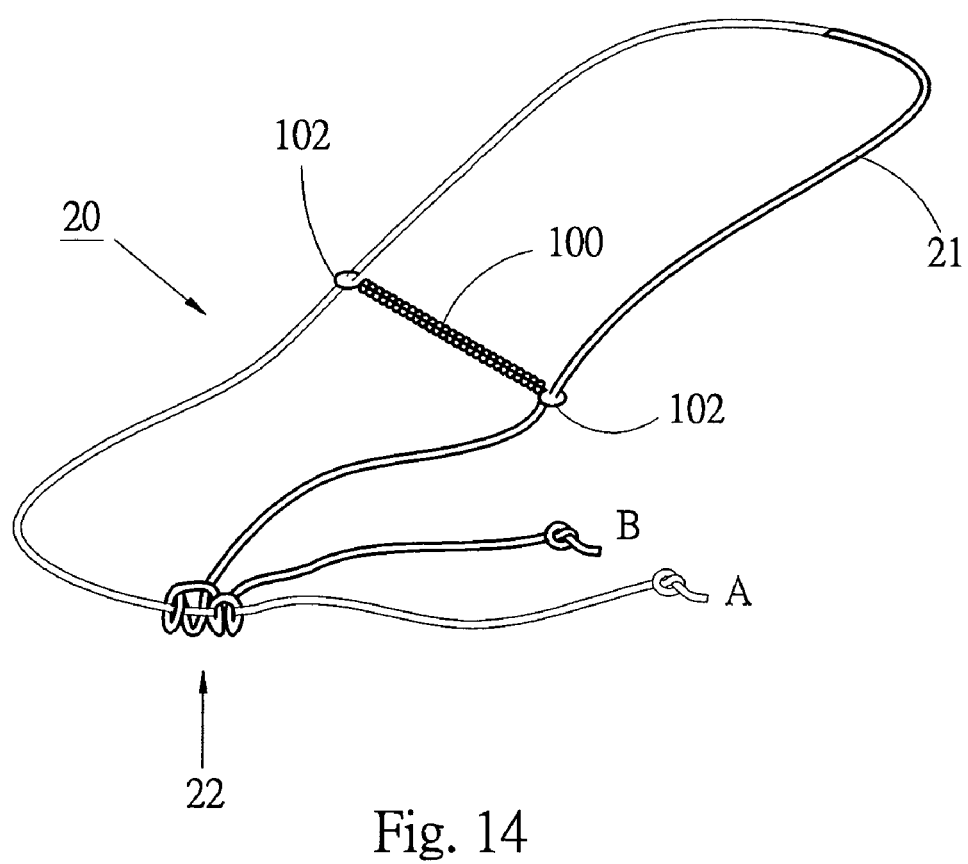
FIG. 14 shows that the locating member is co-used with the loop ligature of the present invention.

The present invention further includes a locating member 100. Referring to FIG. 14, the locating member 100 is like a slender rod formed of a copper filament coated by a plastic skin. Two ends of the copper filament protrude from the plastic skin to form two deformable hook sections 102.

Figure 15:
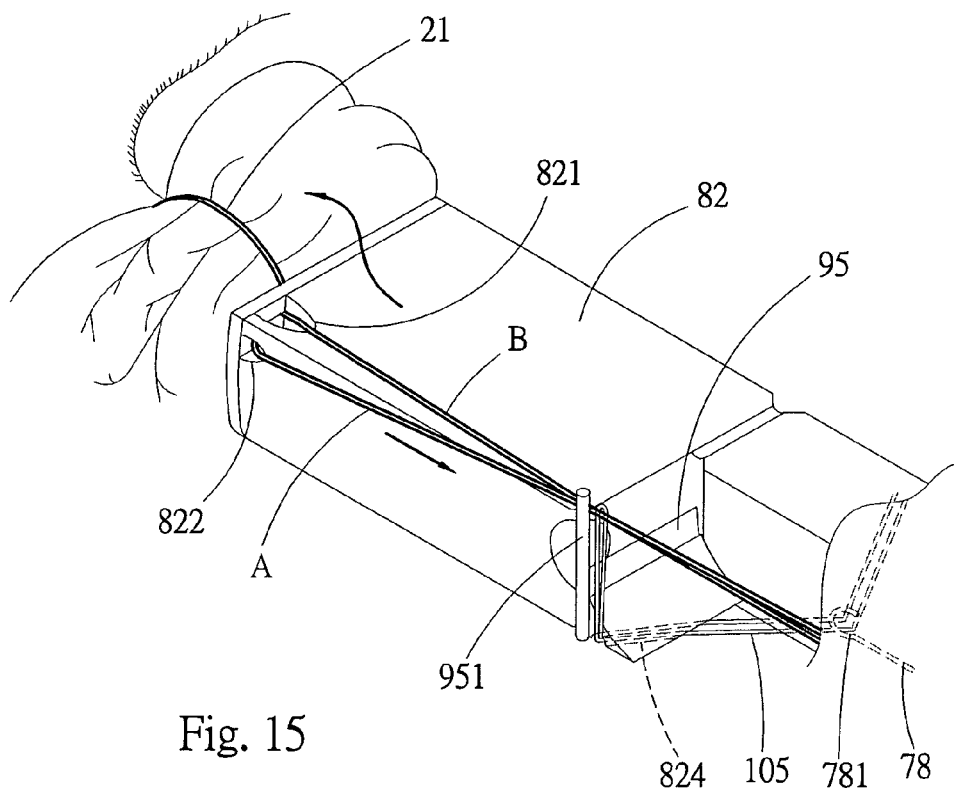
FIG. 15 is a perspective view of a part of the present invention, showing the relative position of the pull member.

The present invention further includes a pull member 105. Referring to FIG. 15, in this embodiment, the pull member 105 is a loop. A middle section of the pull member 105 is hooked with the hook section 781 of the front end of the third tracking member 78. Two ends of the pull member 105 are respectively conducted through the guide channels 824 of the bottom faces of the lower jaws and reversely upward folded for tracking the suture.

Figure 16:
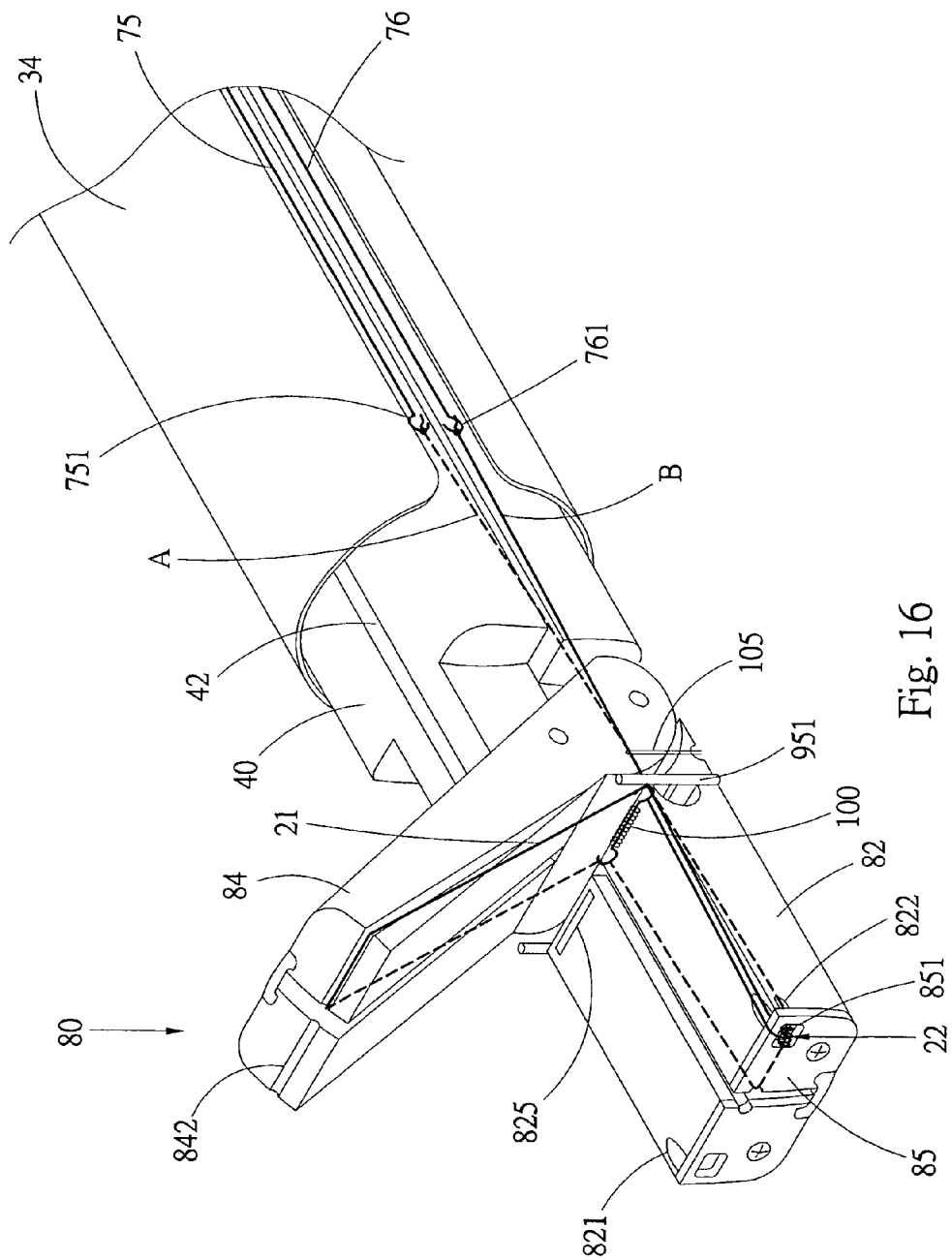
FIG. 16 shows that the loop ligature is loaded in the forceps mouth.

The loop ligature 20 is mounted in the upper and lower jaws 82, 84. Referring to FIG. 14, the loop 21 is first adjusted to a size adapted to the size of the jaws. Then the hook sections 102 of the locating member 100 are hooked with two sides of the loop. Then, as shown in FIG. 16, the upper edge of the loop 21 is inlaid in the grooves 842 of the upper jaws 84 and the locating member 100 is inlaid in an insertion dent 825 formed on rear end of top face of the lower jaw. Then the two ends A, B of the loop ligature 20 are threaded through the through hole 851 of the steel plate 85. The movable end A is conducted rearward through the small groove 822. The fixed end B is conducted through the recess 821. The knotted section 22 of the loop ligature 20 is located in the through hole 851 of the steel plate and the recess 821. The lower edge of the loop 21 is wound along the circumference of the lower jaw 82. The periphery of front end of the lower jaw (or steel plate) can be formed with notch 852 for locating the lower edge of the loop. Accordingly, two loop ligatures 20 can be respectively located on the two pairs of jaws 82, 84.

Then, the two ends A, B of the loop ligature 20 are conducted through one end of the pull member 105 as shown in FIG. 15. The hook section 751 of the first tracking member 75 is hooked with a secure knot of the movable end A of the loop ligature 20 as shown in FIG. 16. The hook section 761 of the second tracking member 76 is hooked with the secure knot of the fixed end B. At this time, the loading of the loop ligature on the forceps of the present invention is completed.

The operation of the present invention in surgery is described as follows:

First, the fixed handle 33 and movable handle 36 of the forceps 30 are held with one hand (such as right hand) to open out the movable handle 36. At this time, the first link 40 is pulled backward to upward open the two upper jaws 84.

Figure 17:
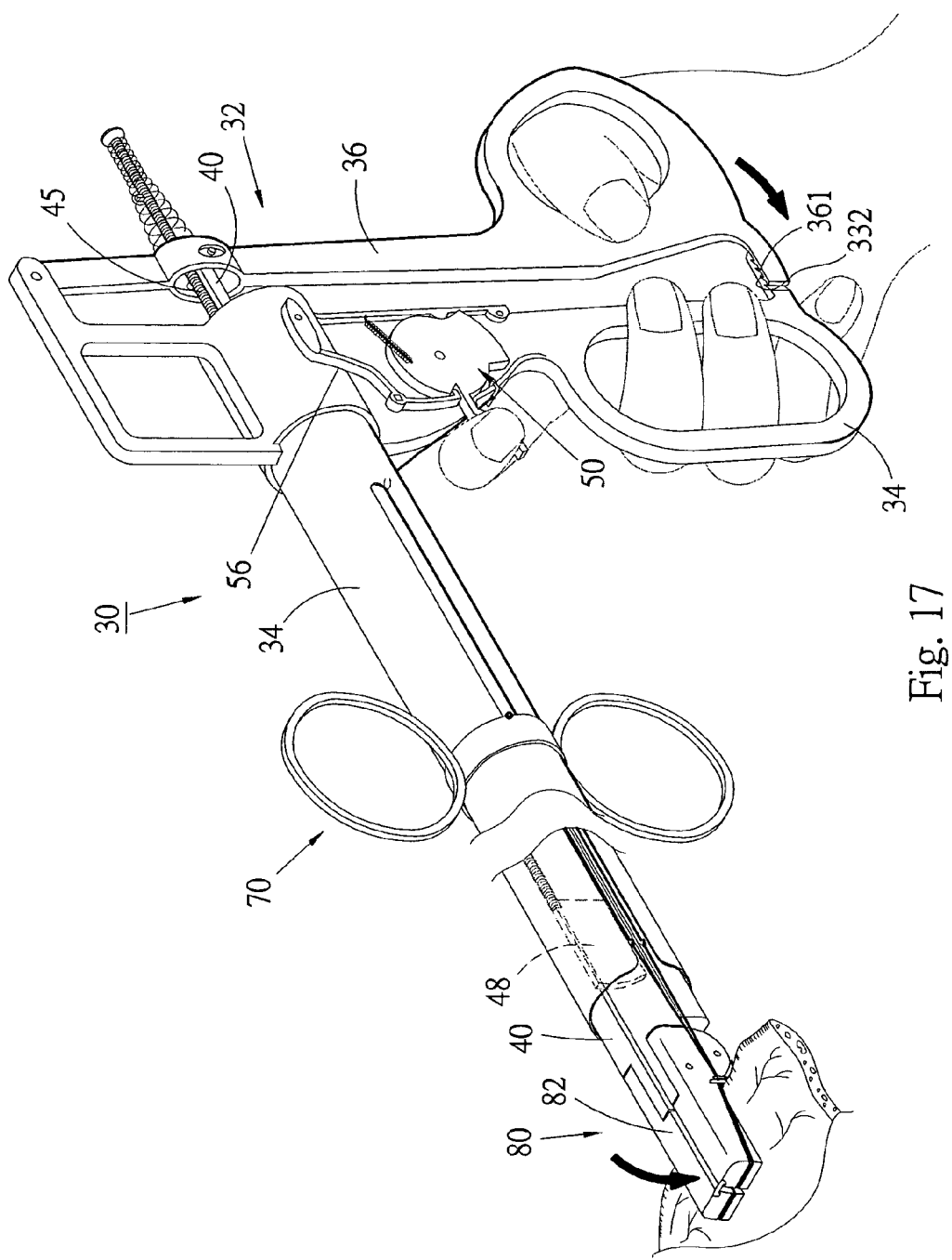
FIG. 17 shows that the forceps of the present invention is operated to clamp a tissue.

The opened forceps mouth 80 is aimed at the tissue to be ligated. Then the movable handle 36 is closed forward as shown in FIG. 17. At this time, the first link 40 drives the upper jaws 84 to close and clamp the tissue in the forceps mouth 80. The bottom of the movable handle 36 has a projection 361 formed with ratchets. The rear end of the fixed handle 33 is formed with ratchets 332. The ratchets can be engaged with each other to keep the handles of the forceps closed.

Figure 18:
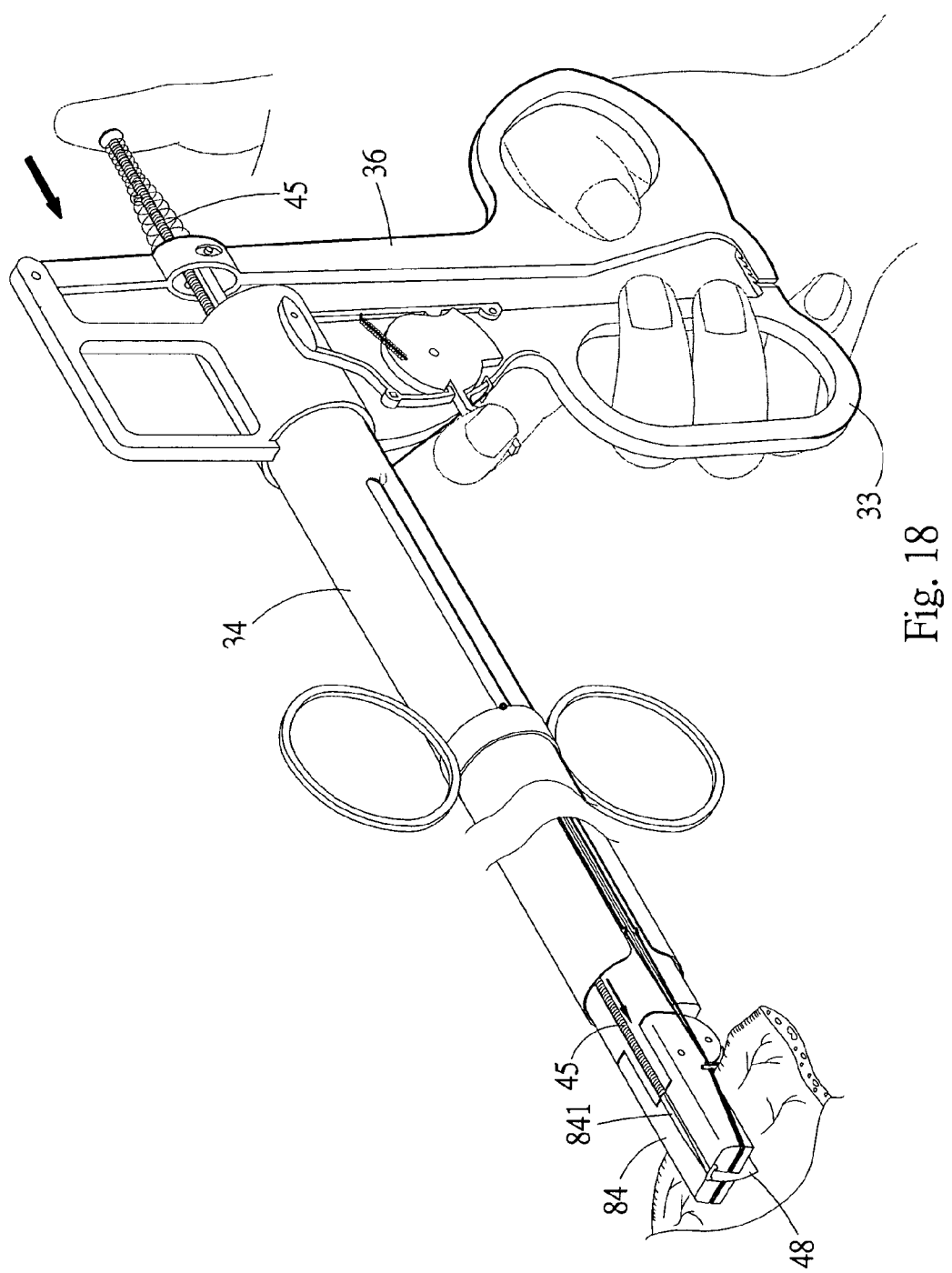
FIG. 18 shows that the forceps of the present invention is operated to incise a tissue.

Then, the second link 45 is forward pushed with the other hand (such as left hand) as shown in FIG. 18. At this time, the blade 48 is moved into the gaps 821, 841 between the two pairs of jaws in front of the front end of the forceps mouth for incising the tissue. In addition, as shown in FIG. 7, a locating member 49 can be disposed on the second link 45 for abutting against back face of the movable handle 36, serving as a front dead end of the travel of the second link. After the second link is released from the pressing force, the first resilient member 46 resiliently pushes back the second link 45, whereby the blade 48 is restored into the fissure 42.

Figure 19:
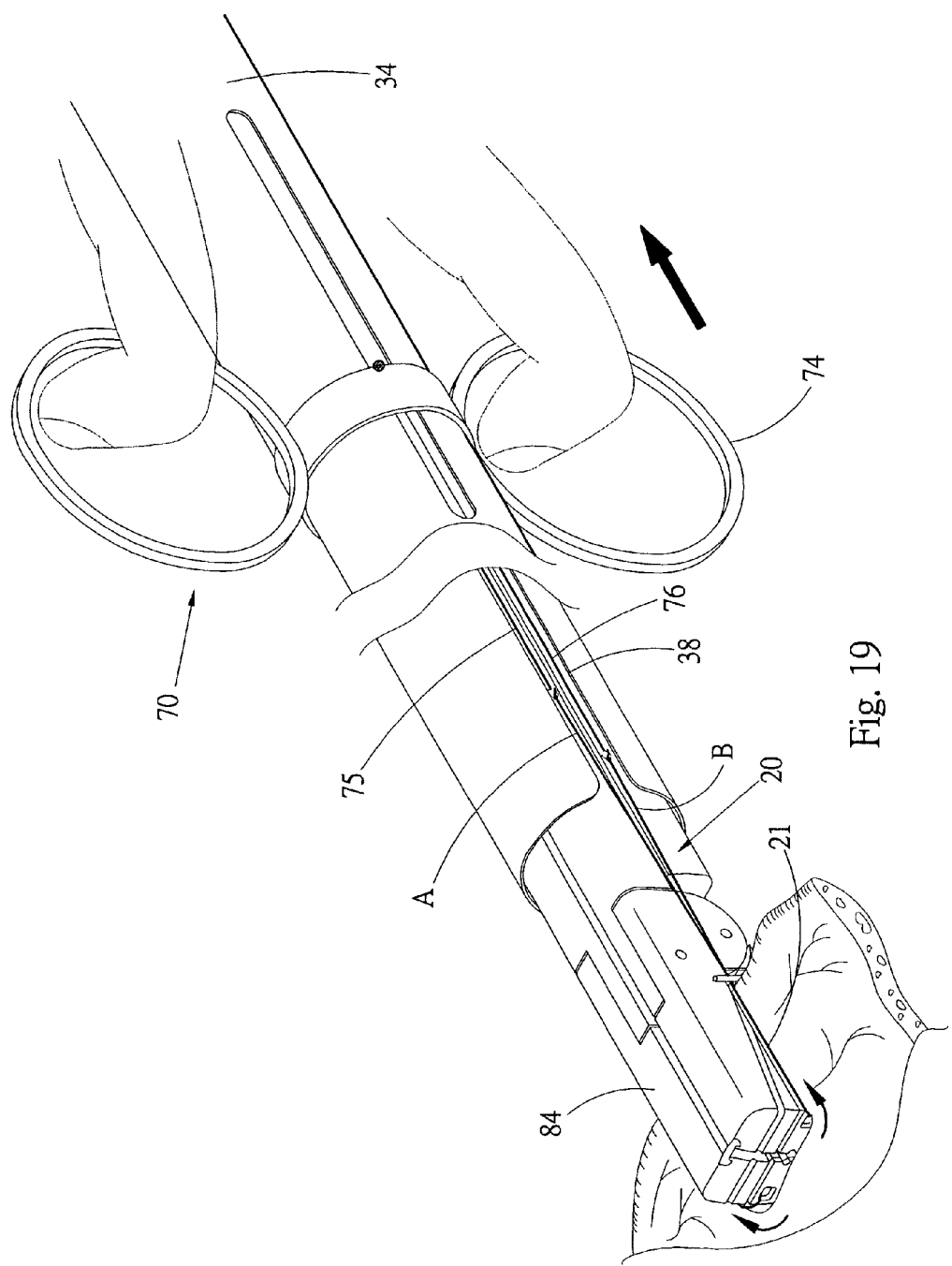
FIGS. 19 and 20 show the divided pedicles are ligated by the loop ligatures.
Figure 20:
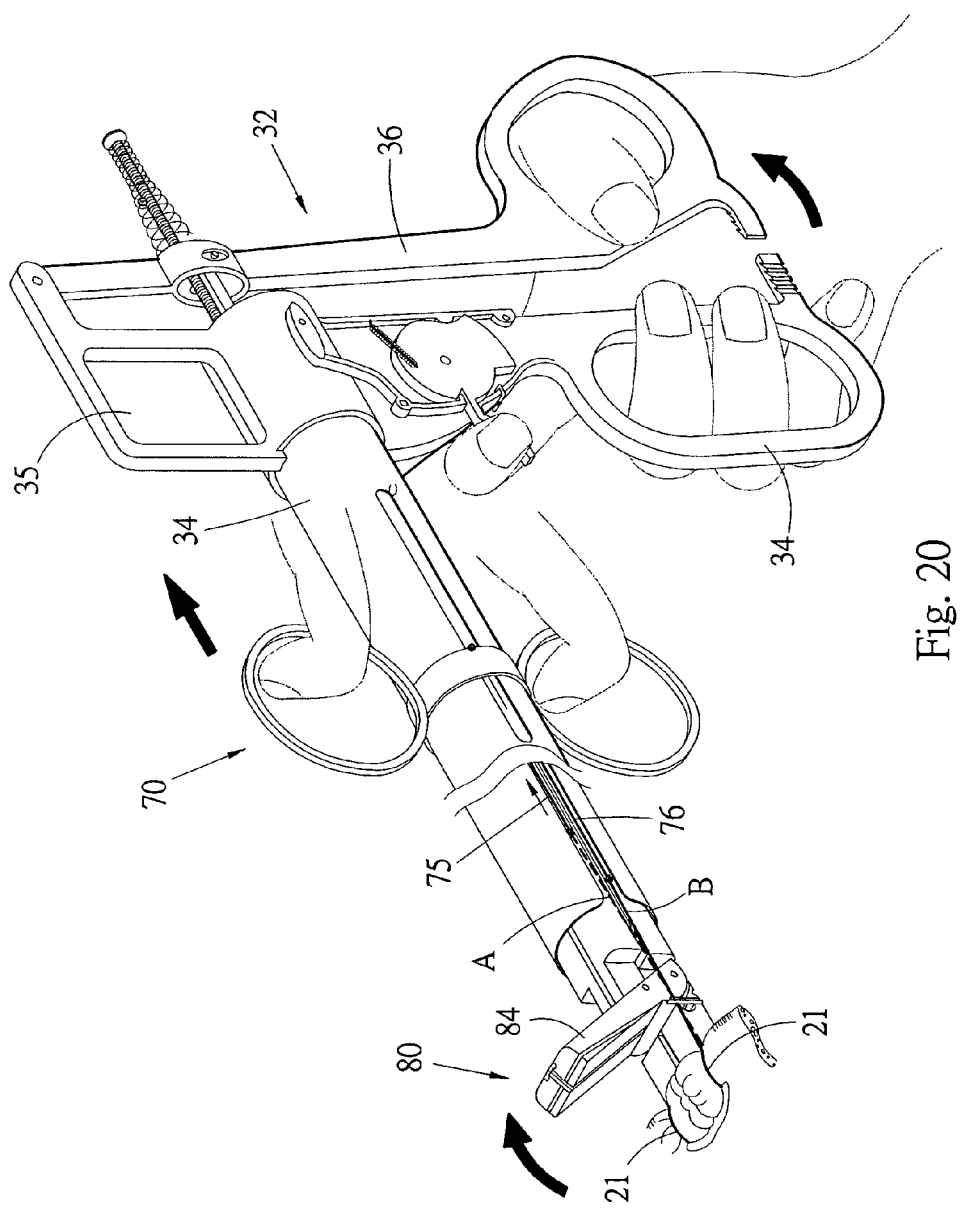

Then, as shown in FIGS. 19 and 20, the thumb of left hand of an operator extends into the finger hole 35 of the forceps body 32 and the index finger and middle finger are respectively extend into the two ring sections 74 of the pull ring 70 to pull the pull ring 70 rearward. Via the two first tracking members 75, the movable ends A of the two loop ligatures 20 are synchronously pulled backward to minify the loops 21 of the loop ligatures. At this time, the hook sections 102 of the locating members 100 are forcedly deformed, whereby the loops are released from the hooked state and separated from the locating members. When the loops are tracked and minified, the loops are separated from the forceps mouth and contracted toward the outer sides of the front ends of the two lower jaws. In addition, when the operator contracts the loops, the loops respectively loop the divided pedicles. Then, as shown in FIG. 20, the operator gradually opens the movable handle 36 with right hand, while continuously pulling the pull ring 70 with left hand so as to ligate the pedicles to a sufficient tensile strength.

Figure 21:
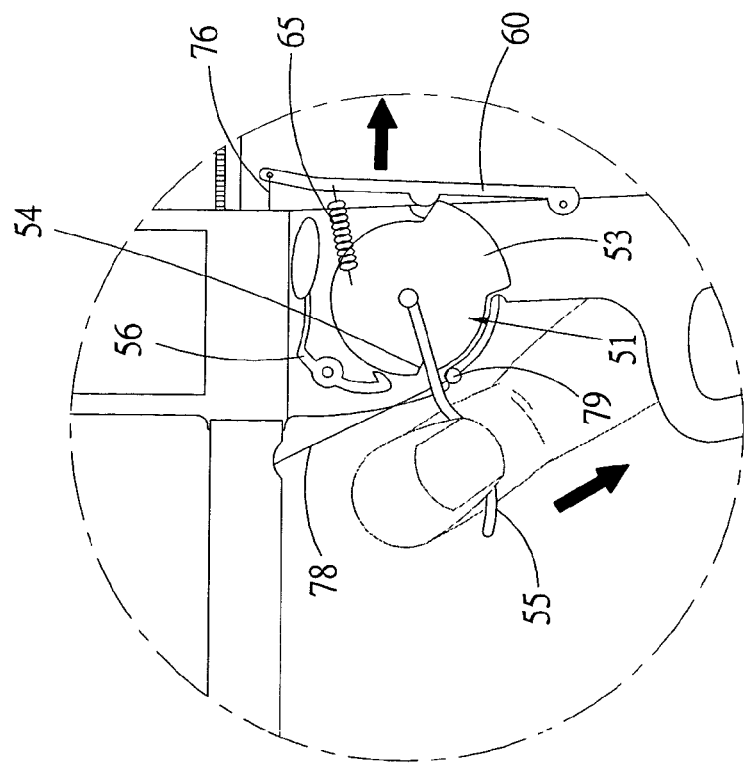
FIG. 21 shows that the trigger is pulled to track the second tracking member.
Figure 24:
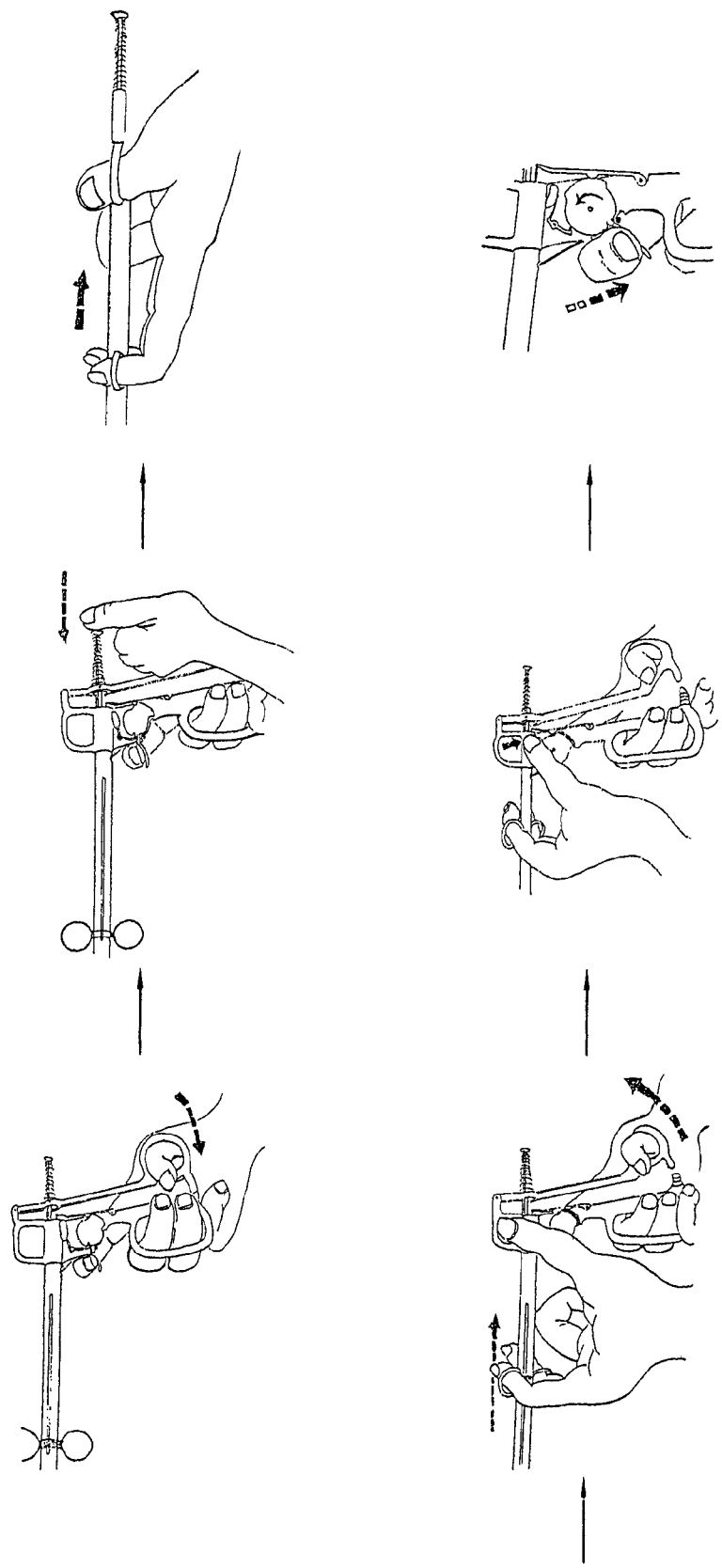
FIG. 24 shows the continuous operations of the present invention, that is, grasping→incision→looping→ligation→securely knotting→cutting residual sutures of post-ligation.

After the above operation is completed, the secure pin 56 is shifted to an unlatched position as shown in FIG. 21. At this time, the secure pin 56 is detached from the notch 54 of the trigger 51. The operator pulls the trigger with index finger of right hand to rotate the body sect ion 52. At this time, the cam sect ion 53 rearward pushes the lever 60, whereby the two second tracking members 76 are synchronously pulled backward by the lever to track the fixed ends B of the two loop ligatures. Accordingly, the loop ligatures are converted into secure knots as shown in FIG. 5 to keep the tensile strength of ligation.

Figure 23:
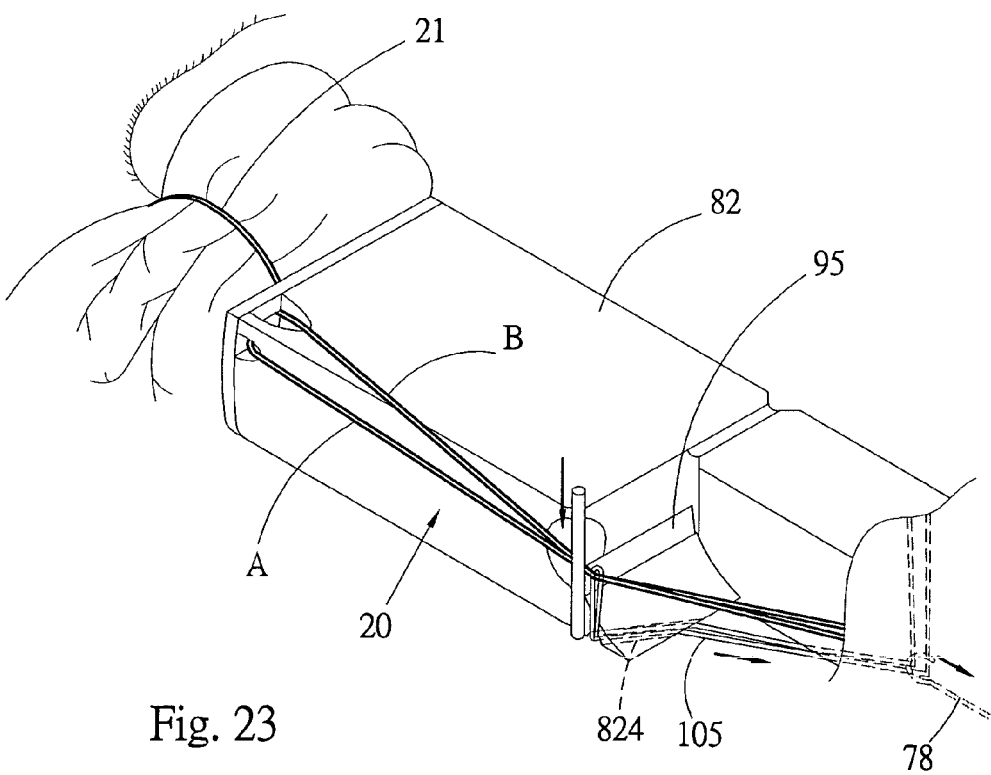
FIG. 23 shows that the residual sutures of post-ligation are cut off.
Figure 22:
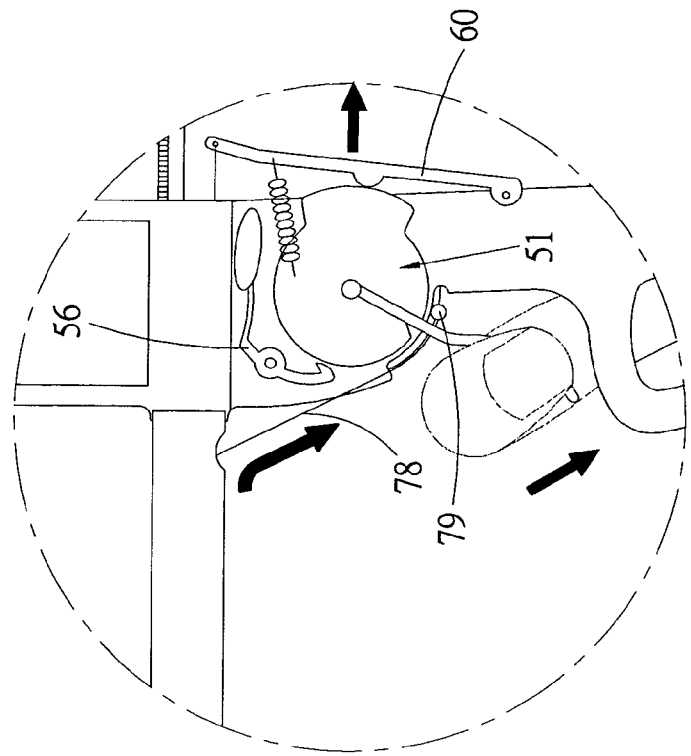
FIG. 22 shows that the third tracking member is drivingly tracked.

When the trigger 51 is further pressed downward, the connecting button 79 is triggered as shown in FIG. 22. At this time, the third tracking member 78 and the pull member 105 are pulled. When the pull member 105 is pulled, two ends thereof respectively downward pull the segments A, B of the loop ligatures 20 as shown in FIG. 23. At this time, the segments A, B are cut off the small blades 95. Accordingly, the residual sutures of post-ligation are smoothly cut off and the forceps set can be removed.

When re-using the forceps set, the operator only needs to load two new loop ligatures onto the forceps mouth.

The forceps set of the present invention can be easily solely operated by an operator. The forceps set of the present invention can rapidly perform the procedures of incision, ligating divided pedicles and cutting residual sutures of post-ligation. In a confined operation field, the forceps set of the present invention can ligate larger and thicker tissue than the existent expensive endoscope instruments. Moreover, the present invention is developed from consolidation of surgical scalpel, forceps and device simulating finger's functions. The present invention enables surgeons to use familiar technique in a challenging operative field such as endoscopic surgery. It will not cost long time for surgeons to learn the operation skill of the forceps set of the present invention. Furthermore, the forceps set of the present invention is a mechanical design without using any special energy so that the surgery can be performed more safely and the operation time is shortened. Therefore, better recovery is achievable.

The above embodiments are only used to illustrate the present invention, not intended to limit the scope thereof. Many modifications of the above embodiments can be made without departing from the spirit of the present invention.

What is claimed is:

1. A multifunctional forceps set comprising:
a forceps body having a fixed handle and a movable handle pivotally connected with rear side of the fixed handle, the movable handle is movable between open and closed positions relative to the fixed handle, a barrel forward extending from the fixed handle;
a first link and a second link fitted in the barrel and slidable along the barrel, a rear end of the first link being pivotally connected with the movable handle and drivingly displaceable by the movable handle, the second link being manually pushable, a blade being fixedly disposed at front end of the second link and positioned in the barrel, wherein the second link controlling a movement of the blade and moving the blade between a front end of the barrel and a retracted position within the barrel;
a press unit disposed on the forceps body and manually pressable to move between a pulled position and a not pulled position;
a pull ring fitted around the barrel and movable along the barrel;
two first tracking members, two second tracking members and a third tracking member all disposed in the barrel and slidable within the barrel, rear ends of the two first tracking members being fixed with the pull ring, whereby when pulling the pull ring toward rear end of the barrel, the two first tracking members are driven and moved rearward, rear ends of the two second tracking members and the third tracking members being connected with the press unit, whereby when pressing the press unit, the second and third tracking members are moved rearward;
a forceps mouth having two lower jaws located side by side and two upper jaws located side by side, the two lower jaws are spaced apart forming a lower gap located there between, and the two upper jaws are spaced apart forming an upper gap located there between, each of the two upper jaws has a circumferential groove extending around a periphery thereof and communicating with the upper gap, the two lower jaws being fixedly disposed at the front end of the barrel, rear ends of the two upper jaws being pivotally connected with rear ends of the two lower jaws which serve as a fulcrum, whereby the upper jaws are movable between open and closed positions relative to the lower jaws and the lower jaws remain in a fixed position relative to the barrel, the front end of the first link being pivotally connected with the rear ends of the upper jaws, whereby when the first link is moved, the two upper jaws are driven and angularly displaced and when the second link is moved forward, the blade extends through the gap between the upper and lower jaws and protrudes from the front end of the forceps mouth;
two small blades disposed at rear ends of the two lower jaws in certain positions; and
a pull member, a middle section of the pull member being connected with front end of the third tracking member, two ends of the pull member being respectively positioned on rear sides of the two lower jaws in certain positions, whereby the pull member is pulled by the third tracking member to displace,
wherein, when the movable handle is located in the closed position, the movable handle moving the upper jaws into the closed position relative to the lower jaws, when the second link is moved forward, the second link moving the blade toward the front end of the barrel, when the pull ring is moved rearwardly, the pull ring retracting the two first tracking members into the barrel, when the press unit is pressed, the press unit retracting the two second tracking members into the barrel, and when the press unit is located in the pulled position, the press unit retracting the third tracking member and pulling the pull member rearwardly.

2. The multifunctional forceps set as claimed in claim 1, further comprising two loop ligatures, each loop ligature being a slippery knot braided from a suture, the loop ligature including a loop, two segments outward extending from the loop and a knotted section braided from the two segments and adjacent to the loop, the knotted section being slippery, whereby when tracking a first segment of the loop ligature, the size of the loop is minified, while when tracking a second segment of the loop ligature, the knotted section is converted into a secure knot, the loops of the loop ligatures being wound along the peripheries of the upper and lower jaws, an end of the first segment being connected with front end of each first tracking member, an end of the second segment being connected with front end of each second tracking member, two ends of the pull member being respectively connected with the two segments of each loop ligature, whereby when the pull member is pulled, the two segments of the loop ligature are driven to move toward the small blades to be cut off by the small blades.

3. The multifunctional forceps set as claimed in claim 2, wherein the front end of each lower jaw is formed with a recess which is slightly larger than the volume of the knotted section of the loop ligature, the front edge of outer side of each lower jaw being formed with a small groove near the recess, the small groove being slightly larger than the diameter of the suture.

4. The multifunctional forceps set as claimed in claim 3, wherein two steel plates are respectively fixedly disposed at front ends of the two lower jaws, each steel plate having a through hole corresponding to the recess.

5. The multifunctional forceps set as claimed in claim 2, further comprising a locating member, two ends of the locating member being respectively formed with two hook sections, the locating member being disposed at rear end of top face of each lower jaw near the pivot joint, two sides of the loop of each loop ligature being respectively hooked with the hook sections of the locating member.

6. The multifunctional forceps set as claimed in claim 5, wherein an insertion dent is formed on rear end of top face of the lower jaw and the locating member is inlaid in an insertion dent.

7. The multifunctional forceps set as claimed in claim 1, wherein the movable handle is formed with a through hole aligned with the rear end of the barrel, the rear end of the first link being pivotally connected in the through hole.

8. The multifunctional forceps set as claimed in claim 1, wherein movable handle is formed with a through hole aligned with the rearend of the barrel, the rear end of the second link extending through the through hole and protruding from rear side of the movable handle, a resilient member being disposed between the rear end of the second link and the movable handle, whereby when no external force is applied to the second link, the second link keeps in a rearward position.

9. The multifunctional forceps set as claimed in claim 1, wherein a fissure is axially formed on the front end of the first link and inward extends from the front end thereof, the fissure being aligned with the gap between the two pairs of jaws, whereby the blade is received in the fissure and displaceable within the fissure and the gap between the two pairs of jaws.

10. The multifunctional forceps set as claimed in claim 1, wherein when pressing the press unit, the second tracking members are first tracked and then the third tracking member is tracked.

11. The multifunctional forceps set as claimed in claim 1, wherein the press unit includes a trigger and a lever, the trigger being pivotally disposed on the forceps body and manually pullable between a pulled position and a not pulled position, the lever being disposed on the forceps body and swingable, whereby when the trigger is pulled, the lever is driven to displace, the rear ends of the two second tracking members being connected with the lever.

12. The multifunctional forceps set as claimed in claim 11, wherein the trigger has a body section and a pull arm connected with the body section, a cam section being formed on a circumference of the body section, the body section of the trigger being pivotally disposed on the fixed handle, whereby the trigger is rotated, the pull arm being for manually shifting, the lever being positioned behind the trigger, whereby when the trigger is positioned in the pulled position, the cam section rearward pushes the lever, a resilient member being disposed between a certain portion of the forceps body and the lever, whereby when no external force is applied to the lever, the lever keeps in a forward leaning state.

13. The multifunctional forceps set as claimed in claim 12, wherein a notch is formed on the circumference of the body section of the trigger, a secure pin being pivotally disposed on the fixed handle and displaceable between a latching position and an unlatching position, whereby when the secure pin is positioned in the latching position, the secure pin hooks the notch of the trigger, while when the secure pin is positioned in the unlatching position, the secure pin unhooks the notch of the trigger.

14. The multifunctional forceps set as claimed in claim 11, wherein after pressing the trigger, the trigger drives and moves the lever to pull and displace the third tracking member.

15. The multifunctional forceps set as claimed in claim 14, further comprising a connecting button displaceably disposed on the forceps body, whereby when the trigger is pulled, the connecting button is driven and moved, the rear end of the third tracking member being connected with the connecting body.

16. The multifunctional forceps set as claimed in claim 15, wherein the connecting button is up and down movable on the fixed handle and positioned right under the trigger, whereby the connecting button is driven and displaced by the trigger.

17. The multifunctional forceps set as claimed in claim 1, wherein outer side of rear end of each lower jaw is formed with an inward extending small fissure, the small blade being disposed in the small fissure.

18. The multifunctional forceps set as claimed in claim 17, wherein a protective jacket is disposed at outer end of each small blade.

19. The multifunctional forceps set as claimed in claim 1, wherein the bottom face of the rear end of each lower jaw is formed with a guide channel; the pull member being flexible, two ends of the pull member being respectively conducted through the guide channels and reversely upward folded through outer sides of the two lower jaws to respectively connect with the sutures of two loop ligatures.

20. The multifunctional forceps set as claimed in claim 1, wherein the two lower jaws are integrally formed at front end of a bar member fixedly disposed in the barrel.

21. The multifunctional forceps set as claimed in claim 1, wherein two slots are formed on two sides of the circumference of a middle section of the barrel, two splits being formed on two sides of front end of the barrel.

22. A multifunctional forceps set comprising:
a forceps body having a fixed handle and a movable handle pivotally connected with the fixed handle, the movable handle is movable between open closed positions relative to the fixed handle, a barrel forward extending from the fixed handle;
a first link and a second link fitted in the barrel and slidable along the barrel, a rear end of the first link being pivotally connected with the movable handle and drivingly displaceable by the movable handle, the second link being manually pushable, a blade being fixedly disposed at front end of the second link and positioned in the barrel, wherein the second link controlling a movement of the blade and moving the blade between a front end of the barrel and a retracted position within the barrel;
a press unit disposed on the forceps body and manually pressable to move between a pulled position and a not pulled position;
a pull ring fitted around the barrel and movable along the barrel;

at least one first tracking member, at least one second tracking member and at least one third tracking member all disposed in the barrel and slidable within the barrel, rear end of the first tracking member being fixed with the pull ring, whereby when pulling the pull ring toward rear end of the barrel, the first tracking member is driven and moved rearward, rear ends of the second tracking member and third tracking member being connected with the press unit, whereby when pressing the press unit, the second tracking member is first driven to move rearward and then the third tracking member is driven to move rearward;

a forceps mouth having two lower jaws located side by side and two upper jaws located side by side, the two lower jaws are spaced apart forming a lower gap located there between, and the two upper jaws are spaced apart forming an upper gap located there between, each of the two upper jaws has a circumferential groove extending around a periphery thereof and communicating with the upper gap, the two lower jaws being fixedly disposed at the front end of the barrel, rear ends of the two upper jaws being pivotally connected with rear ends of the two lower jaws, whereby the upper jaws are movable between open and closed positions relative to the lower jaws and the lower jaws remain in a fixed position relative to the barrel, the front end of the first link being pivotally connected with the rear ends of the upper jaws, whereby when the first link is moved, the two upper jaws are driven and angularly displaced and when the second link is moved forward, the blade extends through the gap between the upper and lower jaws and protrudes from the front end of the forceps mouth;

two small blades disposed at rear ends of the two lower jaws in certain positions; and a pull member connected with the front end of the third tracking member, two ends of the pull member being respectively positioned on rear sides of the two lower jaws in certain positions, whereby the pull member is pulled by the third tracking member to displace, wherein, when the movable handle is located in the closed position, the movable handle moving the upper jaws into the closed position relative to the lower jaws, when the second link is moved forward, the second link moving the blade toward the front end of the barrel, when the pull ring is moved rearwardly, the pull ring retracting the first tracking member into the barrel, and when the press unit is pressed, the press unit retracting the second tracking member first, and then retracting the third tracking member and pulling the pull member rearwardly

* * * * *